United States Patent
John et al.

(10) Patent No.: US 10,239,053 B2
(45) Date of Patent: Mar. 26, 2019

(54) DISPERSED NOBLE METAL-CONTAINING CATALYST FOR HYDROCARBON CONVERSION

(71) Applicant: BHARAT PETROLEUM CORPORATION LIMITED, Mumbai Maharashtra (IN)

(72) Inventors: Mathew John, Uttar Pradesh (IN); Yogesh Suresh Niwate, Uttar Pradesh (IN); S. A. Kishore Kumar, Uttar Pradesh (IN); Shivanand Mukund Pai, Uttar Pradesh (IN); Bharat Lakshman Newalkar, Uttar Pradesh (IN)

(73) Assignee: Bharat Petroleum Corporation Ltd., Mumbai Maharashtra (IN)

( * ) Notice: Subject to any disclaimer, the term of this patent is extended or adjusted under 35 U.S.C. 154(b) by 320 days.

(21) Appl. No.: 14/902,690

(22) PCT Filed: Jun. 23, 2014

(86) PCT No.: PCT/IB2014/001145
§ 371 (c)(1),
(2) Date: Jan. 4, 2016

(87) PCT Pub. No.: WO2015/001404
PCT Pub. Date: Jan. 8, 2015

(65) Prior Publication Data
US 2016/0167028 A1    Jun. 16, 2016

(30) Foreign Application Priority Data
Jul. 2, 2013 (IN) .......... 2243/MUM/2013

(51) Int. Cl.
| | | |
|---|---|---|
| B01J 29/06 | (2006.01) | |
| B01J 29/74 | (2006.01) | |
| B01J 29/068 | (2006.01) | |
| B01J 29/67 | (2006.01) | |
| B01J 29/44 | (2006.01) | |
| B01J 37/08 | (2006.01) | |
| B01J 37/00 | (2006.01) | |
| B01J 35/00 | (2006.01) | |
| B01J 37/04 | (2006.01) | |
| B01J 37/02 | (2006.01) | |
| C07C 5/27 | (2006.01) | |

(52) U.S. Cl.
CPC ......... *B01J 29/7492* (2013.01); *B01J 29/068* (2013.01); *B01J 29/44* (2013.01); *B01J 29/67* (2013.01); *B01J 29/74* (2013.01); *B01J 29/7484* (2013.01); *B01J 35/0066* (2013.01); *B01J 37/0009* (2013.01); *B01J 37/0018* (2013.01); *B01J 37/0236* (2013.01); *B01J 37/04* (2013.01); *B01J 37/08* (2013.01); *B01J 37/086* (2013.01); *C07C 5/2791* (2013.01); *B01J 2229/18* (2013.01); *B01J 2229/186* (2013.01); *B01J 2229/20* (2013.01); *B01J 2229/34* (2013.01); *C07C 2529/74* (2013.01)

(58) Field of Classification Search
CPC . B01J 29/068; B01J 29/44; B01J 29/67; B01J 29/7461; B01J 29/7484; B01J 29/7492; B01J 29/74; B01J 2229/186; B01J 2229/34; B01J 35/0066; B01J 37/0009; B01J 37/0018; B01J 37/086; B01J 37/04; B01J 37/08; B01J 37/0236
USPC .................................. 502/60, 64, 66, 74, 85
See application file for complete search history.

(56) References Cited

U.S. PATENT DOCUMENTS

| | | |
|---|---|---|
| 4,209,384 A | 6/1980 | Hilfman |
| 4,434,311 A * | 2/1984 | Buss ............... B01J 29/605 585/430 |
| 4,568,656 A | 2/1986 | Poeppelmeier et al. |
| 4,814,306 A | 3/1989 | Von Ballmoos et al. |
| 6,528,031 B1 * | 3/2003 | Park ............... B01D 53/8628 423/239.2 |
| 7,141,529 B2 | 11/2006 | Biscardi et al. |
| 2013/0008827 A1 * | 1/2013 | Nagayasu ........... B01J 29/7461 208/64 |

FOREIGN PATENT DOCUMENTS

| | | |
|---|---|---|
| EP | 0 145 289 B1 | 8/1982 |
| EP | 2 554 259 | 2/2013 |

OTHER PUBLICATIONS

International Search Report for PCT/IB2014/001145 dated Oct. 21, 2014, three pages.
Written Opinion of the ISA for PCT/IB2014/001145 dated Oct. 21, 2014, five pages.
Van den Broek et al., "Preparation of Highly Dispersed Platinum Particles in HZSM-5 Zeolite: A Study of the Pretreatment Process of $[Pt(NH_3)_4]^{2+}$" Journal of Catalysis 167, pp. 417-424 (1997).

* cited by examiner

*Primary Examiner* — Elizabeth D Wood
(74) *Attorney, Agent, or Firm* — Nixon & Vanderhye P.C.

(57) ABSTRACT

A method for modification of pretreated acidic porous material via selective cation exchange using suitable solvent to obtain higher noble metal dispersion is described herein. The solvent system required for cation exchange should have its dielectric constant in the range of 25-45, wherein this solvent property is found to impart significant effect on cation loading and distribution, which in turn defines the stability, dispersion of the noble metals. The catalyst so obtained has higher noble metal dispersion and when used for hydroisomerization reaction, leads to higher selectivity even at significantly high conversion values.

10 Claims, No Drawings

DISPERSED NOBLE METAL-CONTAINING CATALYST FOR HYDROCARBON CONVERSION

This application is the U.S. national phase of International Application No. PCT/IB2014/001145 filed 23 Jun. 2014 which designated the U.S. and claims priority to IN Patent Application No. 2243/MUM/2013 filed 2 Jul. 2013, the entire contents of each of which are hereby incorporated by reference.

TECHNICAL FIELD

The subject matter described herein in general relates to a process for preparation of a catalyst involving selective exchange of metal ion complexed with a ligand on to a pre-treated acidic porous material in presence of solvents having specific dielectric constant to ensure a higher dispersion when loaded with noble metals. The present disclosure further relates to a process for producing dispersed noble metal-containing catalyst for hydrocarbon conversion.

BACKGROUND OF THE INVENTION

Supported noble metal catalysts are used in a large number of commercially important applications including hydrogenation, dehydrogenation, isomerization, naphtha reforming, hydrocracking, oxidation, automotive exhaust catalysts, and fuel cells. The catalytic activity of metallic sites of these catalysts depends upon (i) number of metal sites (ii) size of metal site (iii) metal support interaction (iv) noble metal cluster orientation (plane). The orientation of noble metal plane is critical for the structure sensitive reactions which involve breaking or making of C—C, N—N or C—O bonds at the metal site.

Hydrogenation/dehydrogenation reactions are of prime importance to refining industry. These reactions are also inevitable part of the hydroisomerization process used for production of high octane gasoline; dewaxed diesel oil and high quality lube oil with excellent cold low properties. Moreover the metal site activity for these catalytic reactions is scarcely influenced by the orientation of noble planes but is strongly dependent on the dispersion and loading of metal sites.

U.S. Pat. No. 4,209,384 describes a method of preparation of a catalyst consisting of platinum metal loaded on to a mordenite-alumina support for hydroprocessing reaction. The catalyst is prepared by incorporating the platinum component with a solution having a pH greater than 6.

U.S. Pat. No. 4,568,656 describes a process for loading platinum on zeolite-L using an aqueous solution containing a platinum salt and a non-platinum metal salt. The non-platinum metal salt is added in certain critical amount to avoid blockage of pores and to ensure that no acid sites are formed during the platinum loading process.

U.S. Pat. No. 7,141,529 discloses a process for isomerization of straight chain or slightly branched paraffins having ten or more carbon atoms using an intermediate pore size molecular sieve modified with metals and additionally loaded with Group VII metal or metals.

EP 0145289 discloses a process for reforming naphtha which employs a reforming catalyst comprising a zeolite containing at least one Group VIII noble metal. The noble metal is highly dispersed throughout the zeolite and the optionally used binder. The reforming catalyst is capable of terminally cracking various organic compounds and exhibits sustained activity maintenance under reforming conditions and improved selectivity for aromatization products.

U.S. Pat. No. 4,814,306 discloses a method for controlled noble metal exchange over zeolite using bulky organic bases by controlling pH during metal loading step.

Highly dispersed platinum particles on HZSM-5 zeolite have been prepared and the effect of pre-treatment process of $Pt(NH_3)_4]^{2+}$ on the dispersion of platinum particles has been studied (Van Santeen et al., *Journal of Catalysis*, 1997, 167, 417).

SUMMARY

The present disclosure relates to a process for preparing a dispersed noble metal-containing catalyst, the process comprising: contacting a pretreated acidic porous material with at least one metal ion complexed with a ligand in a solvent having dielectric constant in a range of 25-45 to obtain a metal ion exchanged acidic porous material; calcining the metal ion exchanged acidic porous material at a temperature of 300-600° C. to obtain a calcined mixture; incorporating the calcined mixture with a noble metal to obtain a noble metal loaded acidic porous material; drying the noble metal loaded acidic porous material to obtain a dried material; extruding 50% w/w to 95% w/w of the dried material with 5% w/w to 50% w/w of a binder material to obtain a extruded catalyst; and calcining the extruded catalyst at 250-400° C. under constant air flow to obtain a dispersed noble metal-containing catalyst having dispersion of over 90%.

The present disclosure further relates to a dispersed noble metal-containing catalyst for hydroisomerization of long chain n-paraffins ranging from $C_{12}$-$C_{40}$ wherein surface acidity is undesirable.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter

DETAILED DESCRIPTION

The present invention now will be described more fully hereinafter. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The subject matter disclosed herein relates to a process for preparing a dispersed noble metal-containing catalyst for hydrocarbon conversion. The present disclosure provides a process for modification of a pretreated acidic porous material via selective cation exchange using suitable solvent to obtain higher noble metal dispersion. The present disclosure further provides a catalyst with higher noble metal dispersion for hydroisomerization reaction leading to higher selectivity even at significantly high conversion values.

An embodiment of the present disclosure provides a process for preparing a dispersed noble metal-containing catalyst, the process comprising: contacting a pretreated acidic porous material with at least one metal ion complexed with a ligand in a solvent having dielectric constant in a range of 25-45 to obtain a metal ion exchanged acidic porous material; calcining the metal ion exchanged acidic porous material at a temperature of 300-600° C. to obtain a calcined mixture; incorporating the calcined mixture with a noble metal 3 to obtain a noble metal loaded acidic porous material; drying the noble metal loaded acidic porous material to obtain a dried material; extruding 50% w/w to 95% w/w of the dried material with 5% w/w to 50% w/w of a binder material to obtain a extruded catalyst; and calcining the extruded catalyst at 250-400° C. under constant air flow to obtain a dispersed noble metal-containing catalyst having dispersion of over 90%.

The present disclosure describes a process for selective exchange of cationic-complexes on to a pretreated acidic porous material in presence of specific solvents to ensure a higher dispersion when loaded with noble metals. Another embodiment of the present disclosure provides a process, wherein the acidic porous material is selected from the group consisting of zeolite, molecular sieve, amorphous silica-alumina, solid acids and mixtures thereof, preferably selected from the group consisting of ZSM-5, ZSM-22, ZSM-23, ZSM-35, and ZSM-48. Yet another embodiment of the present disclosure relates to a process, wherein the acidic porous material is pretreated by converting the Na-form of the acidic porous material to obtain the H-form of the acidic porous material. The acidic porous material is pretreated by first converting the Na-form of acidic porous material to the H-form by ion exchange with ammonium nitrate followed by calcination at 500° C.

A cation or combination of cations in the form of cationic complex is exchanged on the pretreated acidic porous material under controlled conditions by adopting shape selective ion exchange concept. The cation used is a group-II A metal or a rare earth metal and the complex is formed using but not limited to a supramolecule selected appropriately so as to embrace cationic species and yet impel a net positive charge. The cation-complex being larger in size does not enter the pretreated acidic porous material pores. Moreover, owing to the size of the cation complex and also the charge associated, the cations tend to get exchanged in a scattered manner over the surface. The surface density of the cations over the surface of the pretreated acidic porous material is dependent on the complex used. The availability of sites for any further exchange at a later stage depends on the extent of exchange on the pretreated acidic porous material surface.

An embodiment of the present disclosure provides a process, wherein the pretreated acidic porous material is selectively exchanged with at least one metal ion complex prior to noble metal loading in order to stabilize and enhance noble metal dispersion. Yet another embodiment of the present disclosure provides a process, wherein the metal ion is selected from the group consisting of Group IIA metals, rare earth metals, and mixtures thereof, preferably selected from the group consisting of $Ca^{2+}$, $Ba^{2+}$, $Mg^{2+}$, $Sr^{2+}$, $La^{2+}$, $Ce^{3+}$ and mixtures thereof. The solvent or media for ion-exchange is selected appropriately to ensure the structural stability of the metal complex in the media. The ion exchange was carried out under constant reflux conditions in an appropriate solvent media. The material so prepared was calcined at 300° C. to remove the ligand fraction. An effective loading of the aforementioned cations on the surface of acidic porous material not only ensures neutralization of acid sites but also helps in anchoring of the noble metal leading to improved dispersion of the noble metal on the acidic porous material surface. The noble metal component of the catalyst performs hydrogenation/dehydrogenation function and could be incorporated into the catalyst system by methods such as ion exchange, impregnation or physical admixture, preferably by ion exchange method.

The cationic complexes were selected so that the complex forming ligand shall be easy to remove on calcination. An embodiment of the present disclosure provides a process, wherein the supramolecule is selected according to the cation size and stability of cation-complex from the group consisting of 1,4,10,13-tetraoxa-7,16-diazacyclooctadecane, 4,7,13,16,21,24-hexaoxa-1,10-diazabicyclo[8.8.8] hexacosane, 4,7,13,16,21-pentaoxa-1,10-diaza-(8,8,5)-tricosane, 4,7,10,16,19,24,27-heptaoxa-1,13-diazabicyclo[11.8.8]-nonacosane and their substituted derivatives. The cation-complexes should have a net positive charge and a large size to ensure that the cation-complex does not enter the zeolite pore, thus selectively neutralizing the undesirable external acid site. An example of such a complex forming ligand is a supramolecule (1,4,10,13-tetraoxa-7,16-diazacyclooctadecane), which are cyclic chemical compounds that consist of a ring containing several ether groups. The oxygen atoms are well situated to coordinate with a cation. The presence of lone pair of electron in oxygen atom makes them capable of having strong interaction with the cation when located at the interior of the ring (Scheme 1).

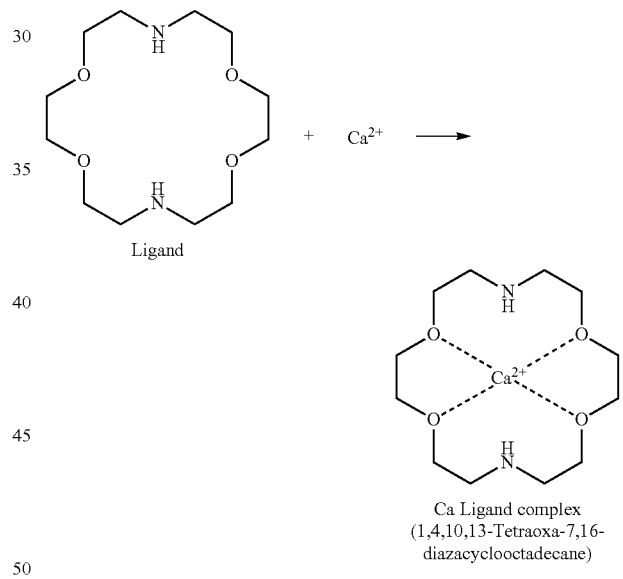

Ca Ligand complex
(1,4,10,13-Tetraoxa-7,16-diazacyclooctadecane)

The key aspect of the metal ion exchanged acidic porous material process is the selection of suitable solvent that maintains the intactness of the cation-ligand complex and also facilitates the proper exchange of complex on the acidic porous material surface. The solvent system required for cation exchange should have its dielectric constants lying between a range of 25-45. An embodiment of the present disclosure provides a process, wherein the solvent is selected from the group consisting of acetonitrile, methanol and mixtures thereof. This solvent property was found to impart significant effect on cation loading and distribution, which in turn defined stability/dispersion of noble metals. Typically used ion-exchange media such as water is not suitable for this purpose as it would readily dissociates the cationic-complex. Non polar solvents such as benzene or toluene did not facilitate proper exchange of the cationic-complex on acidic porous material surface. Surprising only some specific solvents having dielectric constant preferably in the range of 30-40 have all these desired properties for exchange of the cationic-complex on acidic porous material surface. Dielectric constant of various solvents is shown in Table 1

TABLE 1

Dielectric constant of various solvents

| SNo | Solvents | Dielectric Constant |
|-----|----------|---------------------|
| 1 | Water | 80 |
| 2 | Acetonitrile | 38 |
| 3 | Methanol | 33 |
| 4 | Iso-propyl alcohol | 18 |
| 5 | Butanol | 18 |
| 6 | Toluene | 2.38 |
| 7 | Benzene | 2.3 |

Metal ion exchanged acidic porous material is then calcined and further exchanged with noble metal to obtain the desired catalyst. An embodiment of the present disclosure provides a process, wherein the noble metal is selected from the group consisting of Group-VIII noble metals and mixtures of Group VIII noble metals, preferably Pt. An embodiment of the present disclosure provides a process, wherein the noble metal is incorporated into the calcined mixture by a method selected from the group consisting of ion exchange, impregnation and physical admixture. Platinum loading on the acidic porous material surface is typically done via $Pt^{2+}$ ion exchange on the acidic porous material surface. Good dispersion of Pt can be obtained by using the ion-exchange method, however, catalyst prepared by such method when used at elevated temperatures, leads to agglomerization of the noble metal into larger crystallites. Thus, reducing the available sites and overall activity of the metallic sites which in turn affects the catalyst performance. In order to avoid such agglomeration, it is required to prevent migration of noble metal at higher temperatures. This could be done via specific confinement of noble metal due to stronger interaction with the surface and thus preventing surface migration. On calcination the ligand part gets removed and when platinum is loaded on to the acidic porous material, it gets exchanged on the left out sites between the Group-IIA or rare earth metal cation exchanged sites. Platinum is later reduced by hydrogen. Noble metal dispersion for the calcined sample is carried out via hydrogen chemisorption method. The Group-IIA or rare earth metal cation helps in anchoring platinum on to the surface but most importantly, this method allows us to selectively tailor acidic porous material surface so that the platinum sites are confined by surrounding Group-IIA or rare earth metal cation which prevents the migration and agglomeration of platinum at elevated temperatures. Loading of Pt to the metal ion exchanged acidic porous material is generally done by using water soluble salts of Pt for e.g., chloroplatinic acid, tetrammineplatinum complexes, platinum chloride. The use of bulky amine complexes such as tetrammineplatinum complex under basic pH conditions is preferred.

Upon successful loading of noble metal, the acidic porous material slurry is filtered by any suitable means and dried. The dried acidic porous material is next combined with the binder material and formed into extrudates. The present disclosure further relates to a process, wherein the binder material is selected from the group consisting of clay, silica, alumina, metal oxide, and mixtures thereof. The relative proportions of the acidic porous material and binder material may vary between 50 to 95% of zeolite and about 5 to 50% of binder material. These extrudates are then calcined at 400° C. under constant air or oxygen flow.

The present disclosure provides a dispersed nobel metal-containing catalyst prepared by the process of preparing a dispersed nobel metal-containing catalyst, the process comprising: contacting a pretreated acidic porous material with at least one metal ion complexed with a ligand in a solvent having dielectric constant in a range of 25-45 to obtain a metal ion exchanged acidic porous material; calcining the metal ion exchanged acidic porous material at a temperature of 300-600° C. to obtain a calcined mixture; incorporating the calcined mixture with a noble metal to obtain a noble metal loaded acidic porous material; drying the noble metal loaded acidic porous material to obtain a dried material; extruding 50% w/w to 95% w/w of the dried material with 5 w/w to 50 w/w of a binder material to obtain a extruded catalyst; and calcining the extruded catalyst at 250-400° C. under constant air flow to obtain a dispersed noble metal-containing catalyst having dispersion of over 90%.

The catalyst so obtained has a higher noble metal dispersion and leads to higher selectivity even at significantly high conversion values when used for hydroisomerization reaction. The dispersed noble metal-containing catalyst Of the present disclosure is used for hydroisomerization of long chain n-paraffins ranging from $C_{12}$-$C_{40}$ wherein surface acidity is undesirable. An excellent Pt dispersion is very much desirable for hydrogenation/dehydrogenation reactions and is of prime importance to refining industry. These reactions are also inevitable part of hydroisomerization process which is used for the production of high octane gasoline; dewaxed diesel oil, and high quality lube oil with excellent cold low properties.

Typically, these isomerization reactions are carried out in presence of hydrogen over a bifunctional catalyst. The bifunctional catalyst has a metal component responsible for dehydrogenation/hydrogenation and an acid function for isomerization/cracking. Herein, the metal component is a Group-VIII metal usually platinum or palladium while the acid function is acidic porous material which could be zeolite, molecular sieve, amorphous, silica-alumina or solid acids selected on the basis of required catalyst activity selectivity and hydrocarbon chain length. Medium pore zeolites (ZSM-12, ZSM-22, ZSM-23, ZSM-35, ZSM-48, ZM-57, SSZ-32, SSZ-20, EU-1, EU-13, KZ-1, KZ-2, Theta-1 etc) and molecular sieves (SAPO-11, SAPO-31, SM-3, SM-6 etc) have been widely used for diesel and lube dewaxing applications.

During the n-paraffin hydroisomerisation process, the paraffin first undergoes dehydrogenation to olefin at metallic site followed by isomerisation to branched olefin at zeolite pore-mouth and then hydrogenation to form saturated branched paraffin which is desirable. If the number of available metallic sites is limited, it would lead to formation of excessive branched olefin which easily undergoes cracking and hence not desirable. Herein, the effect of selective surface cation exchange on metal dispersion is studied on the basis of hydrogen chemisorption and n-hexadecane isomerisation reaction. Dispersion of metallic site plays a critical role on paraffin isomerisation.

Catalyst was loaded into a fixed bed micro-reactor operated in an upflow mode. Hexadecane feed along with hydrogen was feed to the reactor using a peristaltic pump to maintain a specified Weight Hourly Space Velocity (WHSV) in the range of 0.7-1.4 $h^{-1}$ and hydrogen to hydrocarbon ratio. The product composition analysis was done using GC-FID and GC-MS results to obtain catalyst selectivity at a desired conversion level.

In another embodiment, the selectivity of the catalyst is defined to be ratio of $C_{16}$ isomer yield to the hexadecane conversion. The acidity of the powder and the extrudate form of the catalyst were measured using Ammonia TPD experiments. The noble metal dispersion data was obtained on the basis of hydrogen chemisorption data. The tailoring of zeolite surface to obtain high dispersion and which in turn helps in several catalytic reactions such as hydroisomersation reaction is described in the invention. The following examples illustrate the process of the present invention.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Example 1

Method of Preparation of Calcium-complex 0.5 g of 1,4,10,13-tetraoxa-7,16-diazacyclooctadecane was dissolved in acetonitrile. An equimolar amount of calcium perchlorate salt, which was vacuum dried for overnight at 160° C., was added into the acetonitrile solution. The mixture was stirred for 4 to 5 h at room temperature and the calcium-complex was precipitated using di-ethyl ether. The product purity was verified on the basis of TLC results.

Example 2

Pt Loading, Binding and Extruding of the ZSM-23 Zeolite Base Catalyst without any Group-II Metal The H-form ZSM-23 with Si/Al ratio of 90 and surface area of 263 $m^2/g$, was used to make extruded Pt-loaded catalyst. 0.05 g of tetra-ammonium platinum nitrate complex was dissolved in 50 ml of distilled water. This solution was taken into a flask and 3.5 g of H-ZSM-23 was added on to it. The pH of the solution was adjusted to be maintained in the range of 9 to 10 using tetra butyl ammonium hydroxide. The product was filtered and dried at 100° C. 50 parts of Pt/H-ZSM-23 crystal were mixed with 50 parts of pseudo-boehmite alumina binder in a muller. Sufficient water and few drops of colloidal alumina (Nayacol AL20) was added to produce an extrudable paste on a 1" diameter extruder. This paste was extruded into 1/16" diameter cylindrical extrudates and then dried in an oven at 130° C. overnight. The dried extrudate was calcined in oxygen at 400° C. and this was named catalyst A.

Example 3

Selective Surface Calcium Ion Exchange, Pt Loading, Binding and Extruding of the Selectively Calcium Exchanged ZSM-23 Zeolite Catalyst The H-form ZSM-23 with Si/Al ratio of 90 and surface area of 263 $m^2/g$, was used for the selective cation exchange with Ca-complex. 0.4 g of Ca-complex was dissolved in 35 ml of methanol. 3.5 g of H-ZSM-23 was taken into a three necked flask equipped with mechanical stirrer and a reflux condenser and the dissolved Ca-complex was charged into it. The ion exchange process was carried out under reflux conditions for 6 h. The solution was filtered and the amount of calcium loaded on the zeolite surface was estimated by titrating the filtrate EDTA as per the standard procedure for determination of calcium content using Patton and Reeder's reagent. The selectively Ca-exchanged ZSM-23 sample was calcined at 300° C. and then loaded with platinum, bounded with alumina, extruded dried and then calcined as per method described in the Example 2 and was named catalyst B.

Example 4

Pt Loading, Binding and Extruding of the Calcium Ion Exchange Using Calcium Nitrate Salt (Unlike Example 2 where Selective Surface Exchange is Done) on ZSM-23 Zeolite Catalyst The H-form ZSM-23 with Si/Al ratio of 90 and surface area of 263 $m^2/g$, was used for the purpose. 3 g of H-ZSM-23 sample was contacted with a solution prepared by dissolving 0.08 g of calcium nitrate in 30 ml of distilled water solution. The ion exchange process was carried out under conditions reflux for 6 h at 100° C. The solution was filtered and then loaded with platinum, bounded with alumina, extruded dried and then calcined as per method described in the Example 2 and was named catalyst C.

Example 5

Effect of Solvent Media on Surface Pre-treatment Step

The H-form ZSM-23 with Si/Al ratio of 90 and surface area of 263 $m^2/g$, was used for the cation exchange with Ca-complex. The cationic-complex exchange procedure as described in Example 3 was followed using different solvents (acetonitrile, benzene, iso-propyl alcohol, butanol) instead of methanol. These Ca-exchanged ZSM-23 samples were loaded with platinum, bounded with alumina, extruded dried and then calcined as per method described in the Example 2 and were named catalyst D, E, F & G based on the solvent used during exchange of cationic-complex i.e, acetonitrile, benzene, iso-propyl alcohol and butanol respectively.

Example 6

Effect of Use of Group I Metal-complex in a Non-Polar Solvent for Surface Pre-treatment Step Potassium-complex was prepared using a procedure similar to that of Example 1. The H-form ZSM-23 with Si/Al ratio of 90 and surface area of 263 $m^2/g$, was used for the cation exchange with K-complex. The cationic-complex exchange procedure as described in Example 3 was followed using different benzene as solvent instead of methanol. The K-exchanged ZSM-23 samples were loaded with platinum, bounded with alumina, extruded dried and then calcined as per method described in the Example 2 and was named catalyst H.

Example 7

Pt Loading, Binding and Extruding of the Potassium Ion Exchange Using Potassium Salt (Unlike Example 6 where Selective Surface Exchange is Done)

Potassium was ion exchanged on ZSM-23 zeolite and was formulated into catalyst as per the procedure described in Example 4. The sample was termed as catalyst I.

Example 8

Effect of Use of Rare Earth Metal-complex in a Non-polar Solvent for Surface Pre-treatment Step Lanthanum-complex was prepared as per the procedure described in Example 1 using lanthanum nitrate salt and 4,7,13,16,21,24-hexaoxa-1,10-diazabicyclo[8.8.8]hexacosane (ligand suitable for lanthanum). The H-form ZSM-23 with Si/Al ratio of 90 and surface area of 263 m$^2$/g, was used for the cation exchange with La-complex. The cationic-complex exchange procedure as described in Example 3 was followed using acetonitrile as ion exchange media. The La-exchanged ZSM-23 samples were loaded with platinum, bounded with alumina, extruded dried and then calcined as per method described in the Example 2 and was named catalyst J.

Example 9

Pt Loading, Binding and Extruding of the Lanthanum Ion Exchange Using Lanthanum Nitrate Salt (Unlike Example 8 where Selective Surface Exchange is Done Using La-complex)

Lanthanum was ion exchanged on to H-ZSM-23 zeolite using lanthanum nitrate solution in water and was formulated into catalyst as per the procedure described in Example 4. The sample was termed as catalyst K.

Example 10

Measurement of Metal Dispersion, Activity and Selectivity for the Prepared Catalyst The dispersion data for various catalyst recipes are tabulated in Table 2.

TABLE 2

Pt dispersion data for various catalyst recipes

| Sample | Cation used for exchange during pre-treatment | Solvent used or cation exchange during pre-treatment | Dispersion |
|---|---|---|---|
| Catalyst A | — | — | 40 |
| Catalyst B | [Ca-complex]$^{2+}$ | Methanol | 97 |
| Catalyst C | Ca$^{2+}$ | Water | 87 |
| Catalyst D | [Ca-complex]$^{2+}$ | Acetonitrile | 99 |
| Catalyst E | [Ca-complex]$^{2+}$ | Benzene | 81 |
| Catalyst F | [Ca-complex]$^{2+}$ | Iso-propyl alcohol | 47 |
| Catalyst G | [Ca-complex]$^{2+}$ | Butanol | 43 |
| Catalyst H | [K-complex]$^{1+}$ | Benzene | 77 |
| Catalyst I | K$^+$ | Water | 75 |
| Catalyst J | [La-complex]$^{3+}$ | Acetonitrile | 95 |
| Catalyst K | La$^{3+}$ | Water | 84 |

All the catalyst recipes were tested for hydroisomerization selectivity using hexadecane as the model feed. 5 g of calcined catalyst extrudate diluted with inert material (quartz) was packed in a stainless steel fixed bed reactor. The catalyst was then dried overnight at 130° C. under nitrogen flow and reduced at 320° C. under a constant H$_2$ flow of 100 ml/min at 60 bar pressure for 5 h. After reduction of the metal, the catalyst was used for hexadecane isomerization reaction. The reaction was carried out at a temperature range of 280-320° C., WHSV of 0.8-1.2 h$^{-1}$, with H$_2$/HC ratio of 1000 at 60 bar pressure. The activity and selectivity data for different catalysts are tabulated in the Table 3.

TABLE 3

Comparison of catalyst A, B, C, D, E, H, I, J, and K based on their n-C$_{16}$ isomerization reaction selectivity.

| Sample | Reaction Temperature (° C.) | Conversion | Isomerisation Selectivity |
|---|---|---|---|
| Catalyst A | 285 | 86 | 58 |
| Catalyst B | 290 | 85 | 83 |
| Catalyst C | 310 | 85 | 76 |
| Catalyst D | 290 | 86 | 83 |
| Catalyst E | 295 | 89 | 74 |
| Catalyst H | 305 | 86 | 73 |
| Catalyst I | 315 | 85 | 70 |
| Catalyst J | 285 | 86 | 82 |
| Catalyst K | 285 | 86 | 70 |

Table 3 shows a comparative analysis of catalyst A, B, C, D, E, H, I, J and K based on their n-C$_{16}$ isomerization reaction selectivity. Catalyst A having lowest dispersion depicted an inferior performance compared to all other catalyst recipes. Catalyst B, D and J wherein selective pre-treatment (prior to noble metal loading) was done using Ca and La-complex with methanol and acetonitrile as ion-exchange media gave the best results as compared to all other catalysts. Catalyst C and H required higher operating temperatures indicative of excessive neutralization of acid sites which is not beneficial. Furthermore, a higher requirement of operating temperature during start of run condition is indicative of an overall reduced catalyst life span. These experiments clearly elicit the advantage of selective zeolite pre-treatment in order to obtain higher.

Although the subject matter has been described in considerable detail with reference to certain preferred embodiments thereof, other embodiments are possible. As such, the spirit and scope of the appended claims should not be limited to the description of the preferred embodiment contained therein.

We claim:

1. A process for preparing a dispersed noble metal-containing catalyst, the process comprising;
    (a) contacting an acidic porous material with at least one metal ion complexed with a ligand in a solvent having dielectric constant in a range of 25-45 to obtain a metal ion exchanged acidic porous material;
    (b) calcining the metal ion exchanged acidic porous material at a temperature of 300-600° C. to obtain a calcined mixture;
    (c) incorporating the calcined mixture with a noble metal to obtain a noble metal loaded acidic porous material;
    (d) drying the noble metal loaded acidic porous material to obtain a dried material;
    (e) extruding 50% w/w to 95% w/w of the dried material with 5% w/w to 50% w/w of a binder material to obtain a extruded catalyst; and
    (f) calcining the extruded catalyst at 250-400° C. under constant air flow to obtain a dispersed noble metal-containing catalyst having dispersion of over 90%,
    wherein the acidic porous material comprises a zeolite.

2. The process as claimed in claim 1, wherein the acidic porous material is selected from the group consisting of ZSM-5, ZSM-22, ZSM-23, ZSM-35, and ZSM-48.

3. The process as claimed in claim 1, wherein prior to step (a) the acidic porous material is pretreated by converting the Na-form of the acidic porous material to obtain the H-form of the acidic porous material.

4. The process as claimed in claim 1, wherein the metal ion is selected from the group consisting of $Ca^{2+}$, $Ba^{2+}$, $Mg^{2+}$, $Sr^{2+}$, $La^{2+}$, $Ce^{3+}$ and mixtures thereof.

5. The process as claimed in claim 1, wherein the ligand is a supramolecule able to form stable metallo-macrocycles with the metal ion.

6. The process as claimed in claim 5, wherein the supramolecule is selected from the group consisting of 1,4,10,13-tetraoxa-7,16-diazacyclooctadecane, 4,7,13,16,21,24-hexaoxa-1,10-diazabicyclo[8.8.8]hexacosane, 4,7,13,16,21-pentaoxa- 1,10-diaza(8,8,5)-tricosane, and 4,7,10,16,19,24,27-heptaoxa-1,13-diazabicyclo[11.8.8]-nonacosane.

7. The process as claimed in claim 1, wherein the solvent is selected from the group consisting of acetonitrile, methanol, and mixtures thereof.

8. The process as claimed in claim 1, wherein the noble metal is selected from the group consisting of Group-VIII noble metal and mixtures of Group-VIII noble metals.

9. The process as claimed in claim 1, wherein the noble metal is incorporated into the calcined mixture by a method selected from the group consisting of ion exchange, impregnation and physical admixture.

10. The process as claimed in claim 1, wherein the binder material is selected from the group consisting of clay, silica, alumina, metal oxide, and mixtures thereof.

* * * * *